(12) United States Patent
Cantor et al.

(10) Patent No.: US 8,246,572 B2
(45) Date of Patent: Aug. 21, 2012

(54) BONE GRAFT APPLICATOR

(75) Inventors: Jeffrey B. Cantor, Ft. Lauderdale, FL (US); Banning G. Lary, Miami, FL (US); Todd P. Lary, Homestead, FL (US)

(73) Assignee: Lary Research & Development, LLC, Miami, FL (US)

( * ) Notice: Subject to any disclaimer, the term of this patent is extended or adjusted under 35 U.S.C. 154(b) by 0 days.

(21) Appl. No.: 12/970,426

(22) Filed: Dec. 16, 2010

(65) Prior Publication Data

US 2011/0152754 A1  Jun. 23, 2011

Related U.S. Application Data

(60) Provisional application No. 61/284,691, filed on Dec. 23, 2009.

(51) Int. Cl.
*A61M 31/00* (2006.01)
(52) U.S. Cl. ................ 604/60; 604/14; 604/15
(58) Field of Classification Search .......... 604/11, 604/14, 15, 18, 57, 59, 13, 16, 17, 60–64, 604/12; 606/92–95, 99, 100
See application file for complete search history.

(56) References Cited

U.S. PATENT DOCUMENTS

| | | | |
|---|---|---|---|
| 1,538,678 A * | 5/1925 | Blinn | 604/59 |
| 4,232,670 A | 11/1980 | Richter et al. | |
| 4,500,310 A * | 2/1985 | Christinger | 604/228 |
| 4,588,395 A | 5/1986 | Lemelson | |
| 5,395,383 A * | 3/1995 | Adams et al. | 606/151 |
| 5,697,932 A | 12/1997 | Smith et al. | |
| 5,925,051 A | 7/1999 | Mikhail | |
| 6,019,765 A | 2/2000 | Thornhill et al. | |
| 6,939,318 B2 * | 9/2005 | Stenzel | 604/60 |
| 7,014,640 B2 | 3/2006 | Kempainen et al. | |
| 7,306,611 B2 * | 12/2007 | Cirotteau et al. | 606/92 |
| 7,513,901 B2 | 4/2009 | Scifert et al. | |
| 2003/0149438 A1 * | 8/2003 | Nichols et al. | 606/99 |
| 2004/0153090 A1 | 8/2004 | Vandewalle | |

OTHER PUBLICATIONS

"closed". American Heritage Dictionary of the English Language. <http://education.yahoo.com/reference/dictionary/entry/closed>.*

* cited by examiner

*Primary Examiner* — Kevin C. Sirmons
*Assistant Examiner* — Kami A Bosworth
(74) *Attorney, Agent, or Firm* — McHale & Slavin, P.A.

(57) ABSTRACT

Disclosed herein is a bone graft applicator assembly including a specially designed applicator, attached to a reservoir of bone graft material, such that the graft material can be moved into the delivery portion while the tip of the delivery portion is in place. The instantly disclosed device allows for the collapse of the delivery tip so that the tip can be placed between vertebras or alternatively within any bony structure or implant where the placement of bone graft material would be desirable, and then expanded to allow the bone graft material to be placed between the vertebras or the like while maintaining the geometry of the space into which the bone graft material is being placed.

8 Claims, 7 Drawing Sheets

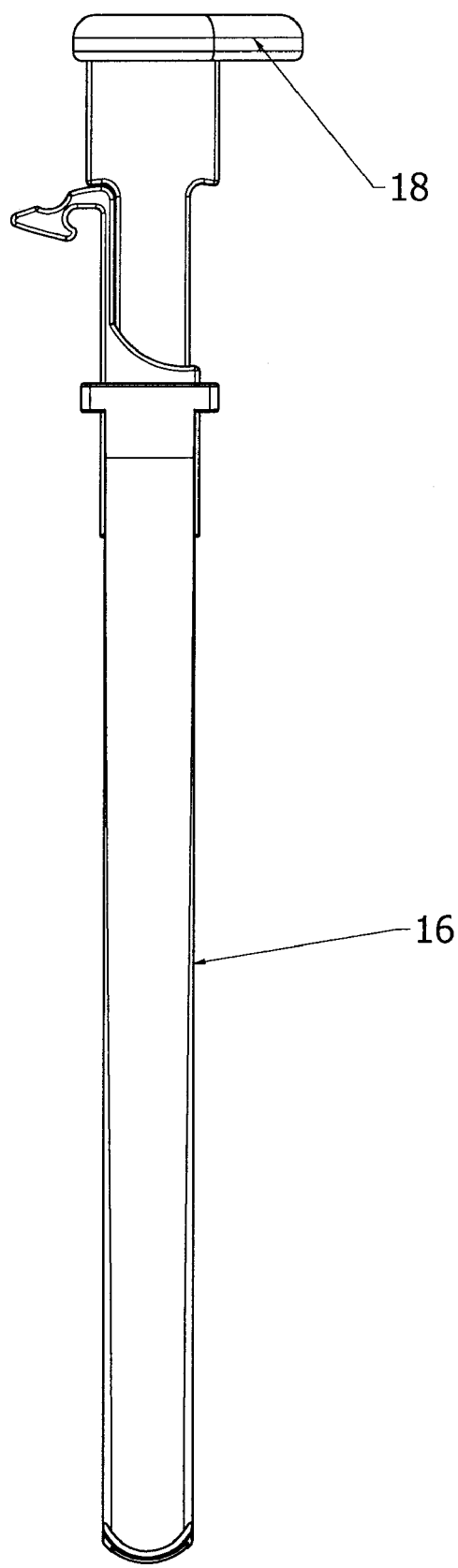
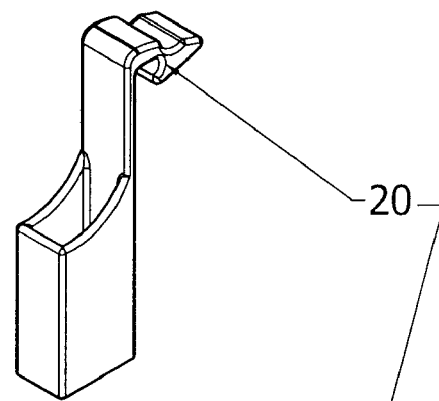
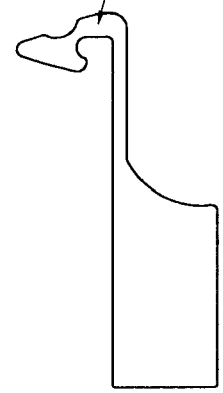
FIGURE 3A
FIGURE 3B
FIGURE 3C

BONE GRAFT APPLICATOR

REFERENCE TO RELATED APPLICATION

This application claims benefit of the filing date of U.S. Provisional Patent Application No. 61/284,691, filed on Dec. 23, 2009, the contents of which is incorporated herein by reference in its entirety.

FIELD OF THE INVENTION

This invention relates generally to devices that are used to deliver bone graft material. Moreover it pertains specifically to a device that is comprised of a bone graft reservoir, plunger and an applicator. Moreover it pertains specifically to collapsible devices that deliver bone graft material to the spinal region. It pertains to an apparatus that will place bone graft material between the vertebras.

BACKGROUND OF THE INVENTION

As opposed to traditional, open spine surgery which involves cutting or stripping the muscles from the spine, it has become common to perform spinal surgery using minimally invasive techniques, a treatment that involves small incisions and muscle dilation, allowing the surgeon to gently separate the muscles surrounding the spine rather than cutting them.

Spinal fusion procedures, such as minimally invasive Lateral Interbody Fusion (XLIF and DLIF), minimally invasive Posterior Lumbar Interbody Fusion (PLIF), minimally invasive Transforaminal Lumbar Interbody Fusion (TLIF), and minimally invasive Posterior Thoracic Fusion are often recommended as a surgical treatment option for patients with a condition causing spinal instability in their lower back, such as degenerative disc disease, spondylolisthesis or spinal stenosis.

In performing such a procedure the surgeon will make a small incision in the skin of the back over the vertebra(e) to be treated. Depending on the instrumentation to be used, the incision could be as small as approximately 3 centimeters. The muscles surrounding the spine will then be dilated to allow access to the section of spine to be stabilized. After the spine is accessed, the lamina (the "roof" of the vertebra) is removed to allow visualization of the nerve roots. The facet joints, which are directly over the nerve roots, may sometimes be trimmed to give the nerve roots more room.

The surgeon will then move the nerve roots to one side and remove disc material from the front (anterior) of the spine. Bone graft material, designed to serve as a bridge, or scaffold is then inserted into the disc space. Screws and rods may then be inserted, if necessary, to stabilize the spine while the treated area heals and fusion occurs. Fusing of the bone graft with the bones of the spine will provide a permanent union between those bones. Bone grafts may be taken from the hip or from another bone in the same patient (autograft) or from a bone bank (allograft). Bone graft extenders and bone morphogenetic proteins (hormones that cause bone to grow inside the body) can also be used to reduce or eliminate the need for bone grafts. The ultimate goal of the procedure is to restore spinal stability.

DESCRIPTION OF THE PRIOR ART

Prior art devices designed to deliver bone graft material to the spine, such as those listed hereinafter, are fixed in nature and do not allow for the collapse of the delivery tip.

Thornhill et al., U.S. Pat. No. 6,019,765, discloses a bone allograft applicator device and system effective to apply a bone graft slurry to an artificial joint without having to remove a previously implanted prosthetic component. In one embodiment, the device includes a hollow member coupled to an actuation mechanism for discharging the bone slurry from the device via a nozzle coupled to a distal end of the hollow member. The device can be used to discharge bone graft slurry from the nozzle and through a screw hole in an acetabular component implanted in the acetabulum of a patient. A bone allograft system can include various components for loading the device with the slurry and/or a plurality of nozzles each having a geometry suited for a particular application.

Lemelson, U.S. Pat. No. 4,588,395, discloses a device for disposing a quantity of matter at a select location within an animal or human body. In one form, the matter is a solid material, such as medication which dissolves with time, a source of radiation such as gamma radiation, a sensor or transducer in a housing which includes a short wave transmitter or other material or device which is operable to beneficially affect human tissue or body function when it is inserted into the body. The material is retained within a housing located at an end of a flexible tube or catheter which is inserted into a body cavity and is manipulated from the other end thereof to a predetermined location within the body cavity. Suitable actuating means located at the external end of the catheter is operated, when the head end thereof is at a predetermined location within the human body, to cause the material supported within the head to be ejected therefrom.

Kemppainen et al., U.S. Pat. No. 7,014,640 B2, is directed toward a dispensing device for granule bone graft of varying and/or irregular shape, characterized by a body defining a handle/hopper portion, a dispensing portion, and a feed system. The subject device permits reloading or refilling of bone graft at the time of use of the device. The bone graft dispensing device also accepts vials of bone graft. The vials are loaded onto and releasably retained by the dispensing device. In both forms, the feed system allows a controlled and/or variable rate of flow of bone graft during dispensing. The subject device may be made disposable as well as re-usable. The subject device is also modular in design allowing easy assembly/disassembly. The subject bone graft dispenser is particularly suited for the dispensing of dry, particulate and/or granule bone graft. Particularly, the bone graft dispensing device is especially suited for the dispensing of particulate or granule bone graft having particulates or granules of various and/or irregular size, shape and combinations thereof.

Mikhail, U.S. Pat. No. 5,925,051, discloses a method and apparatus for introducing and compacting bone graft material in an enlarged femoral cavity including a dispenser having a barrel containing bone graft material and a cannulated ejector/compactor positionable over a multi-section guide wire for both ejecting bone graft material from the barrel and compacting the bone graft material while being guided on the guide wire. The ejector/compactor has a modular head which may be removed and replaced by other heads of varying size.

Smith et al., U.S. Pat. No. 5,697,932, discloses a surgical technique for the delivery of bone graft to a medullary canal and implantation of a prosthetic device including placing bone graft into an elongate hollow tube and arranging a plunger having an elongate rod portion into the hollow tube. The hollow tube, bone graft and plunger assembly are inserted into the medullary canal which has been prepared for the assembly by reaming the medullary canal with a reamer corresponding in size to the hollow tube. The hollow tube is withdrawn from the medullary canal while the plunger is pushed into the canal, resulting in bone graft exiting the hollow tube and being packed by the plunger. A trial prosthesis is used to shape the bone graft within the canal for the prosthesis. Space for a cement mantle can be left through the use of an appropriately sized trial prosthesis.

Scifert et al., U.S. Pat. No. 7,513,901 B2, discloses a graft syringe assembly for delivering bone graft material. The graft syringe assembly comprises a syringe subassembly including a syringe barrel having an inner chamber adapted for receiving bone graft material, a plunger adapted for expelling bone graft material from the inner chamber, the plunger slidably received within the inner chamber, and a syringe adapter coupled to the syringe barrel. The graft syringe assembly further comprises a connection subassembly coupled to the syringe adapter, and a delivery tube subassembly coupled to the connection subassembly, wherein the connection subassembly is configured to allow the delivery tube subassembly to rotate relative to the syringe subassembly.

Richter et al., U.S. Pat. No. 4,232,670, discloses a tubular supply container for use in a medical syringe to dispense bone cement having a pipe formed tube with a slidable plunger. A smaller diameter injection pipe is removably secured to the forward end of the pipe formed tube. A funnel may also be applied to the forward end of the tube to assist in filling the container or may be placed on the rear end to serve as a stand.

Vandewalle, U.S. Pat. No. 2004/0153090 A1, discloses a method and apparatus to apply a selected material to the intramedullary canal of a selected bone. The apparatus generally includes a reservoir area from which the selected material can be expressed. The apparatus further includes an outlet or nozzle which allows for directing of the material as it is being expressed from the reservoir. Further, the apparatus allows the material to be expressed into the intramedullary canal during a procedure involving the intramedullary canal. The apparatus obviates forming an additional incision to apply the material.

If a bone graft delivery applicator could be provided wherein the applicator has a collapsible tip which is adapted for placement between the vertebrate, and then expanded to perform both a distraction and a delivery function, thereby enabling positioning of the graft material between vertebral bodies, a long felt need in the art would be realized.

SUMMARY OF THE INVENTION

The present invention provides a specially designed applicator, attached to a reservoir of bone graft material, such that the graft material can be moved into the delivery portion while the tip of the delivery portion is in place. The instantly disclosed device allows for the collapse of the delivery tip so that the tip can be placed between vertebras or alternatively within any bony structure or implant where the placement of bone graft material would be desirable, and then expanded to allow the bone graft material to be placed between the vertebras or the like while maintaining the geometry of the space into which the bone graft material is being placed.

Accordingly, it is a primary objective of the instant invention to provide a bone graft applicator assembly useful for inserting a bone graft material with a bony structure or implant.

It is a further objective of the instant invention to provide a bone graft applicator assembly which is suitable for placing bone graft material within an area via a minimally invasive technique.

It is yet another objective of the instant invention to provide an applicator assembly which maintains the geometry of the space during insertion of the bone graft material.

It is a still further objective of the invention to provide a kit inclusive of a funnel, variously sized applicators, variously sized and shaped spacers, and appropriately sized plungers, to enable the surgeon to pick and choose from a variety of parts and create therefrom the bone graft applicator assembly best suited to the particular patient's anatomical requirements.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

FIG. 3A illustrates an embodiment of an insert with plunger inserted therein;

FIG. 3B is a perspective view focusing on an embodiment of an attachment tab for affixing the insert to the funnel body;

FIG. 3C is a side view of the attachment tab of FIG. 3B;

DETAILED DESCRIPTION OF THE INVENTION

As will be explained in detail, with reference to the associated figures, a specially prepared applicator has been designed to provide for the traveling path of the bone graft material in relation to the vertebras to ensure a complete delivery to the desired location.

Figure 1:
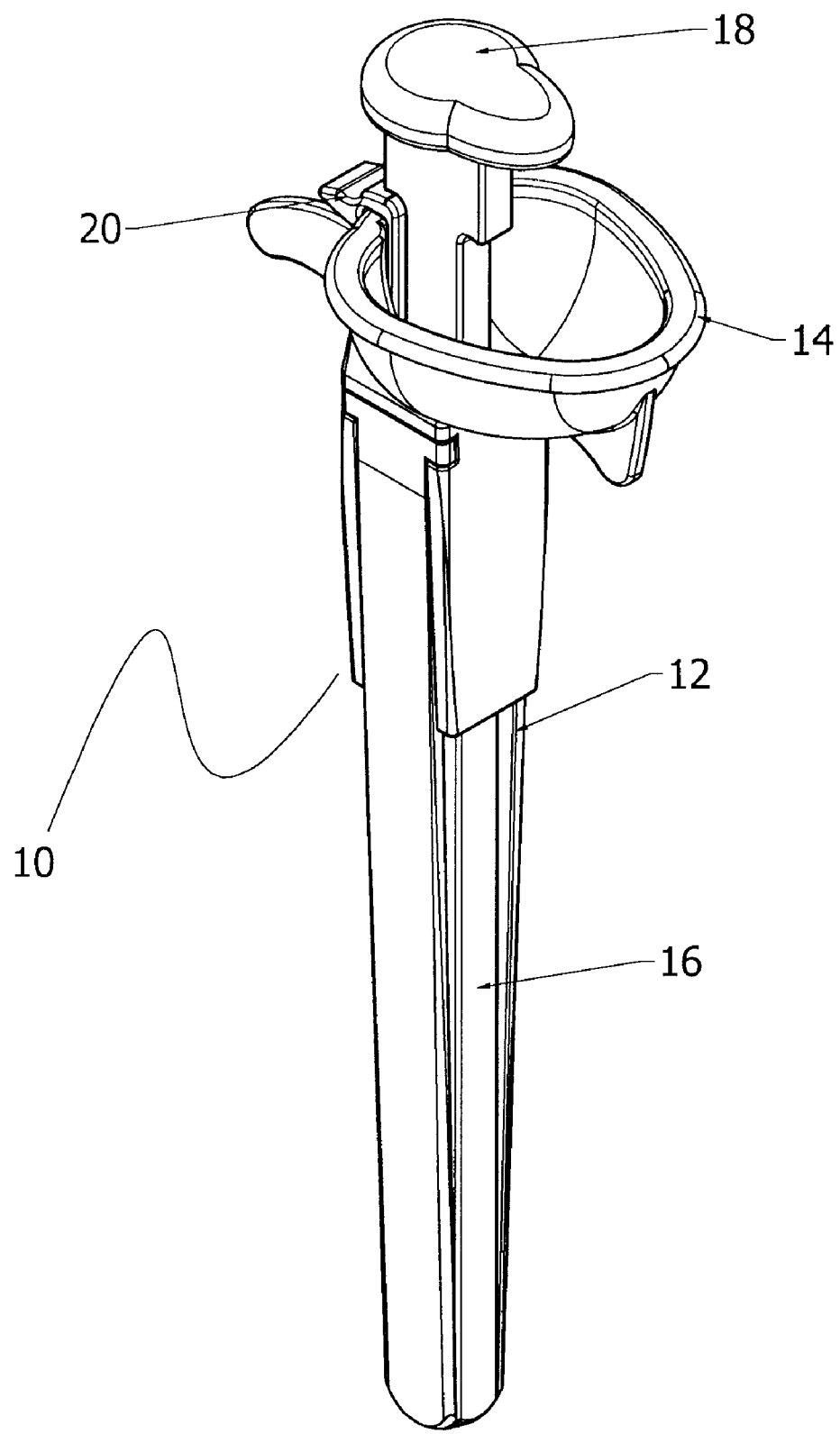
FIG. 1 illustrates a perspective view of a fully assembled bone graft applicator.

With reference to FIG. 1, a bone graft applicator assembly, generally referred to by the numeral 10, includes applicator tabs 12, a bone graft reservoir/funnel 14, an insert 16 and a plunger 18. The components of the bone graft applicator assembly 10, acting in concert, are designed to provide a predetermined path for the plunger 18 to travel. In addition, the components are designed in such a manner as to allow easy transfer of bone graft material (not shown) from the reservoir 14 to the applicator tabs 12. Bone graft material may be taken from the hip or from another bone in the same patient (autograft) or from a bone bank (allograft). Bone graft extenders and bone morphogenetic proteins (hormones that cause bone to grow inside the body) can also be used to reduce or eliminate the need for bone grafts.

The reservoir and applicator combination are hereinafter referred to as the applicator assembly. Applicator 10 is comprised of a pair of applicator tabs 12 which may be coupled to reservoir 14 or formed as a unitary device therewith. The applicator is designed and fabricated from such a material that will allow flexibility in the operation of the device, e.g. titanium, stainless steel, a polymeric material, nitinol, or the like. The design of the funnel 14 that incorporates the applicator tabs 12 is angled in such a way as to position the distal ends of the applicator tabs 12 in a "collapsed" state so that the distal tips are together. The applicator 10 is designed to allow entry of the collapsed distal ends thereof into the incision (not shown) while maintaining sufficient rigidity to ensure proper placement of the bone graft material; while at the same time, providing maximum view-ability of the opening to allow optimal placement of the applicator tip in a collapsed state. Once the tip is located in the proper position the applicator is expanded to a similar geometry of the plunger 18 to enable the operator to experience a tactile feedback of the resistance of the graft material as it enters the incision, not impeded by the walls of the applicator. Expansion of the applicator is effectuated by an insert 16 that defines the geometry of the expanded distal end of the applicator. Insert 16 may constitute a variety of different shapes which can be inserted into the applicator to provide different geometries. Upon being fully inserted, insert 16 can be attached to funnel 14 via latching tab 20 so as to form a secure connection while the bone graft material is being inserted. In a particular embodiment, the ends of the applicator tabs may be shaped, e.g. rounded or the like, to cooperate most efficiently with the space into which the bone graft material is to be inserted.

Figure 2:
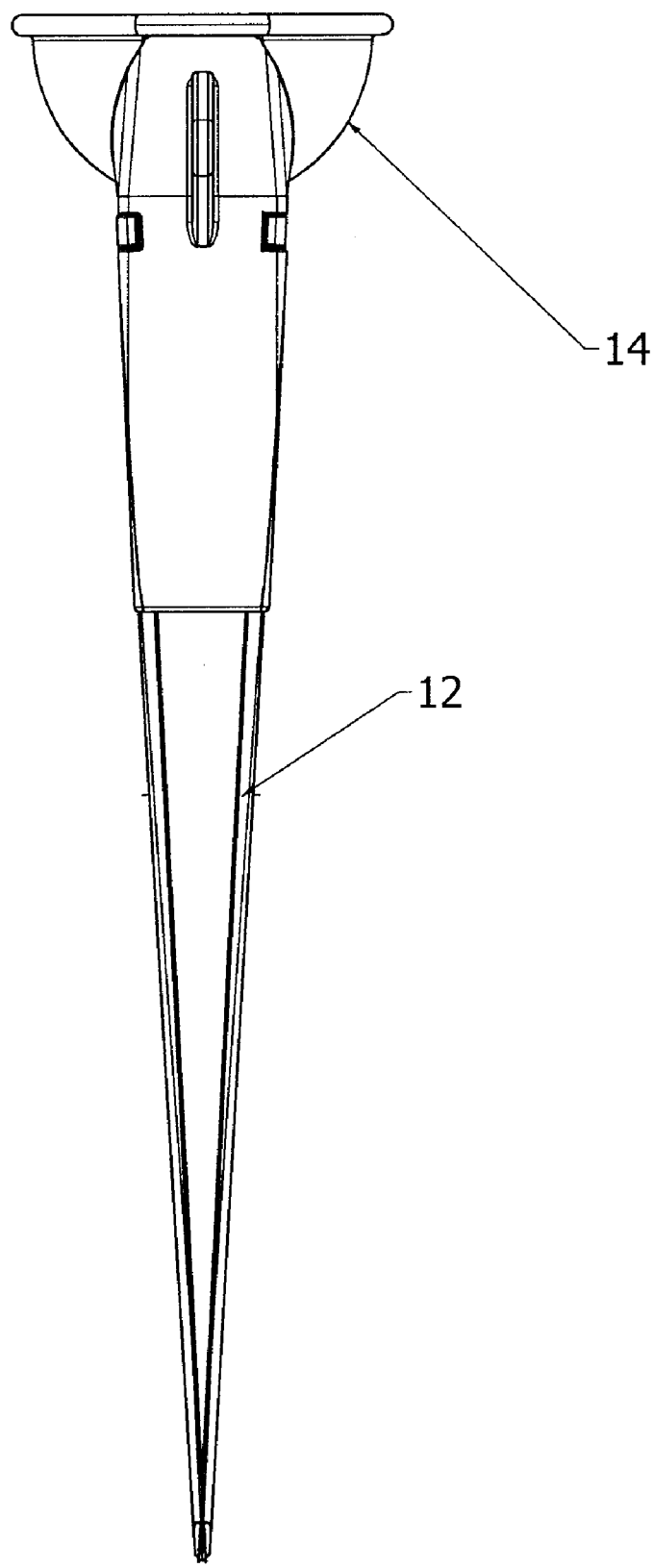
FIG. 2 illustrates an embodiment of a funnel reservoir with tabs in a normal orientation biased together.

With reference to FIG. 2, an embodiment of an applicator assembly is illustrated having a funnel 14 and applicator tabs 12, wherein the applicator tabs are shown in their normal orientation of being biased together at their distal ends so as to be in contact in a generally V-shaped configuration.

Referring now to FIG. 3A, the cooperation of insert 16 and plunger 18 is illustrated. FIGS. 3B and 3C more particularly shows the details of the top end 20 of insert 16 whereby it is adapted to attach to the rim of funnel 14.

Figure 4:
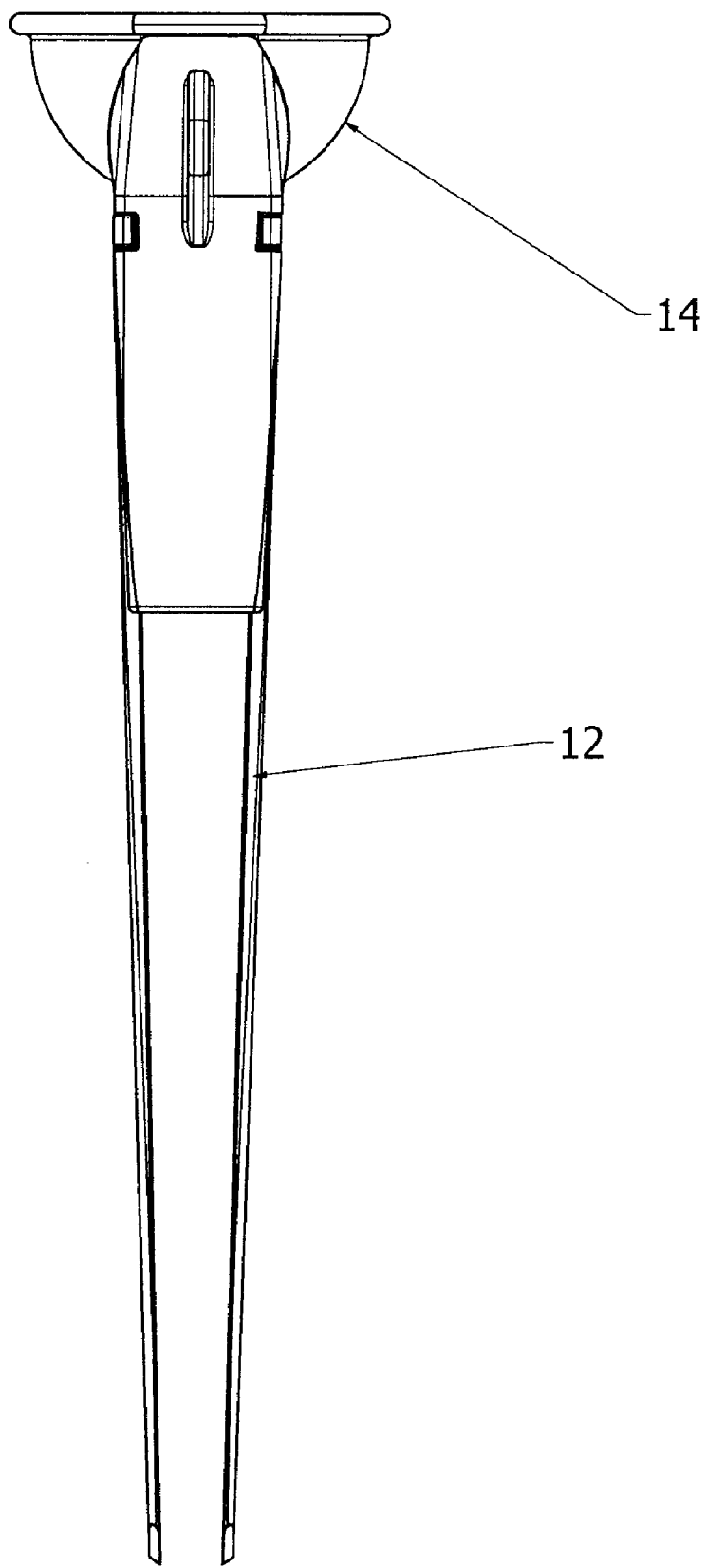
FIG. 4 illustrates an embodiment of a funnel reservoir with tabs spaced apart.

FIG. 4 is now referenced, as it illustrates an embodiment of the applicator assembly wherein the funnel 14 is show engaged with the applicator tabs 12, which are shown with the tabs splayed apart, as they would be subsequent to receipt of the insert 16, therebetween.

Figure 5:
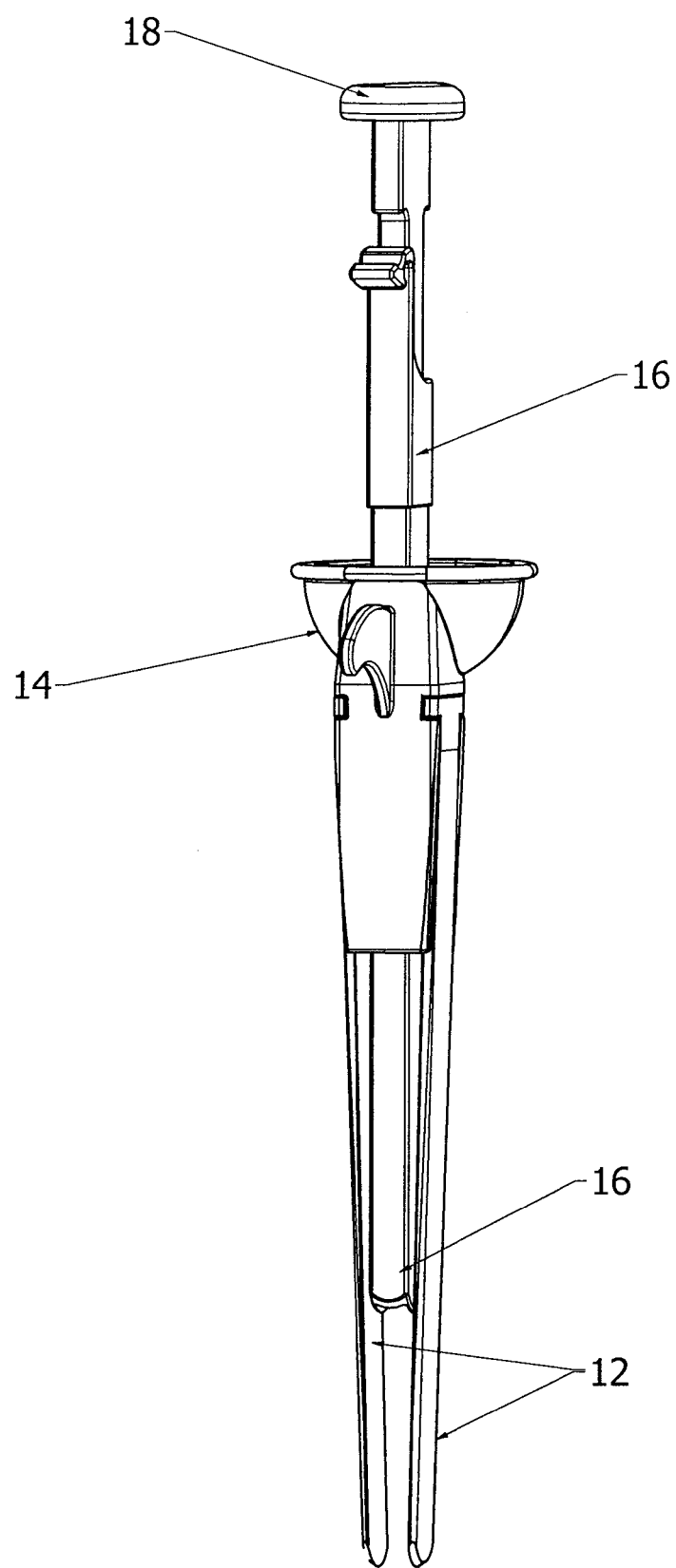
FIG. 5 is an alternative embodiment illustrating a plunger and insert combination inserted within a funnel.

Referring now to FIG. 5, funnel 14 is shown in a stage of assembly wherein insert 16 has been placed between applicator tabs 12 and plunger 18 is shown in position within insert 16. Once the plunger 18 and insert 16 have been positioned such that the insert 16 is locked onto the funnel 14 the plunger 18 may be removed and then reinserted, whereby bone graft material contained in the funnel 14 can be urged to the desired intervertebral space, or the like space within a bony structure or implant where bone graft material placement is desirable.

Figure 6:
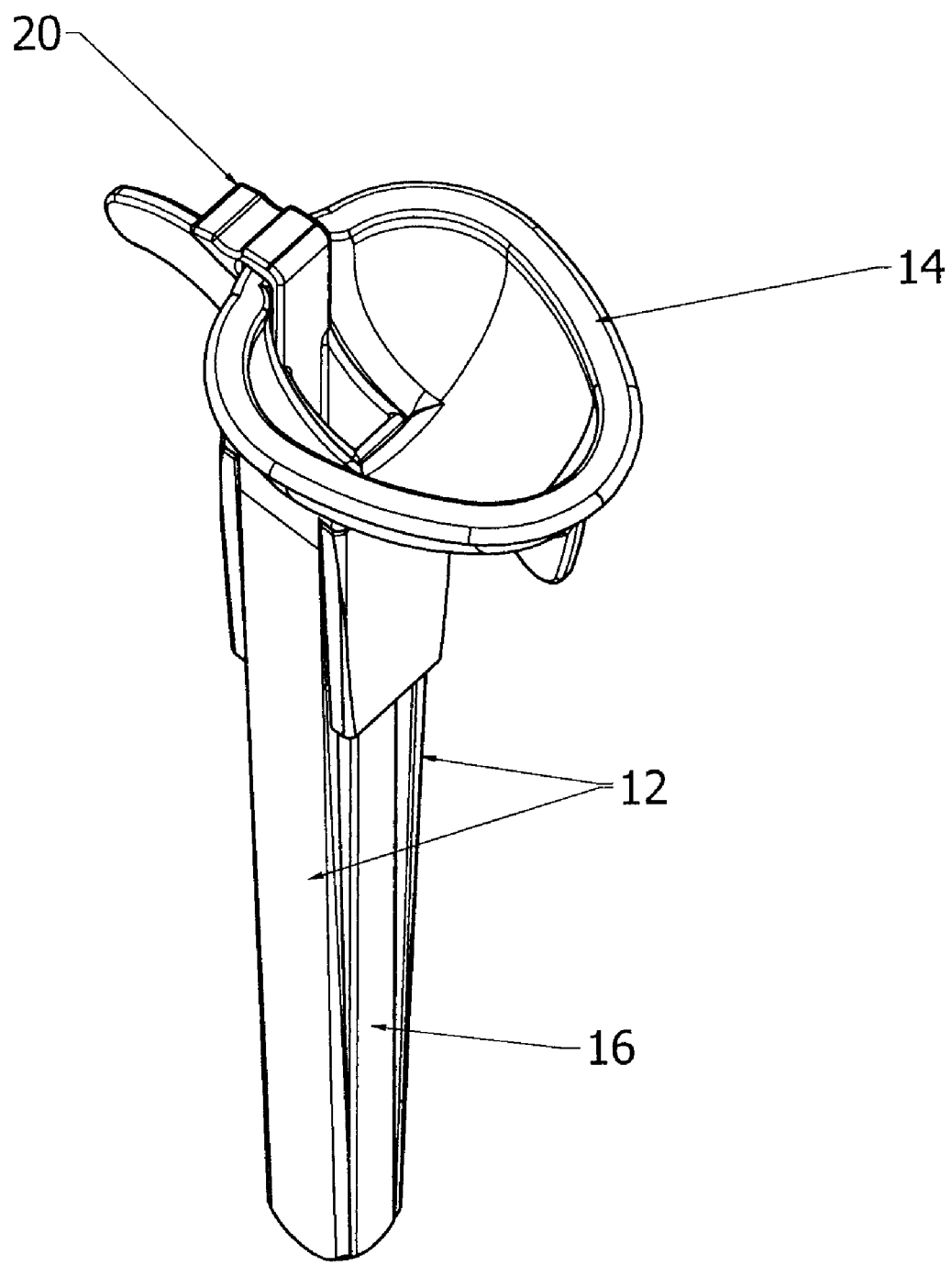
FIG. 6 is illustrative of the combination of FIG. 5 with the plunger removed.

With reference to FIG. 6, an illustration is provided of an embodiment of an applicator assembly wherein the insert has been positioned between the applicator tabs 12.

Figure 7:
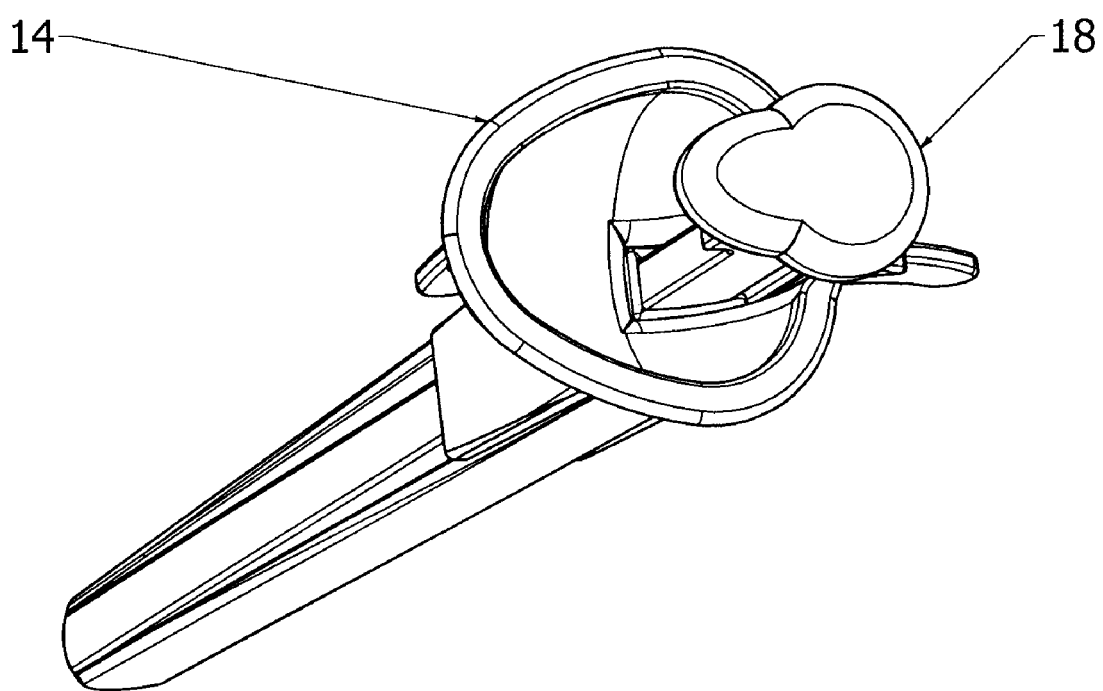
FIG. 7 is a top perspective view illustrating the insertion of the plunger within a funnel embodiment.

FIG. 7 illustrates insertion of plunger 18 into the aperture therefore in funnel 14.

It is a understood that it is within the purview of this invention to provide a kit inclusive of a funnel, variously sized applicators, variously sized and shaped spacers, and appropriately sized plungers, to enable the surgeon to pick and choose from a variety of parts and create therefrom the bone graft applicator assembly best suited to the particular patient's anatomical requirements.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A bone graft applicator assembly useful for inserting bone graft material within or between one or more bony structures or implants comprising:

an applicator assembly having a proximal end and a distal end, said proximal end being in the form of a funnel having attached directly thereto or formed therewith a pair of applicator tabs which extend from said funnel to said distal end of said assembly, said applicator tabs traversable between a first position defined by a distal end of one of said applicator tabs being biased toward a distal end of said other applicator tab to contact said distal end of said other applicator tab in said first position, thereby forming a closed end which is insertable within or between one or more bony structures or implants and a second position defined by said distal ends being separated by a degree of expansion defined by the size of an insert positioned therebetween, said degree of expansion thereby forming and maintaining a space for insertion of bone graft material;

an insert having a proximal end, a distal end, and an internal lumen there between adapted for receipt of a plunger, said insert adapted to be positioned between said applicator tabs, said insert having a particular size and shape which acts to define said degree of expansion of said applicator tabs upon insertion therebetween; and a plunger for urging bone graft material along a path defined by said applicator tabs and said insert;

whereby said bone graft material when inserted within said applicator assembly is guided toward said bony structure or implant along said path defined by said applicator tabs and said insert.

2. The bone graft applicator assembly of claim 1 wherein said applicator assembly is constructed and arranged such that said applicator tabs are positioned together at said distal ends thereof to form a generally V-shaped configuration.

3. The bone graft applicator assembly of claim 1 wherein said bone graft applicator assembly further includes a latching tab formed at the proximal end of said insert for providing a secure connection to said funnel.

4. The bone graft applicator assembly of claim 1 wherein said insert is sized and shaped to direct said bone graft material within a space created by the traversal of said applicator tabs from said first closed position to said second position.

5. A kit for facilitating placement of bone graft material within or between one or more bony structures or implants comprising:

at least one funnel for receipt of a bone graft material and one or more pairs of applicator tabs of varying length and shape adapted to directly engage said at least one funnel, said applicator tabs traversable between a first position defined by a distal end of one of said applicator tabs being biased toward a distal end of said other applicator tab to contact said distal end of said other applicator tab in said first position, thereby forming a closed end which is insertable within or between one or more bony structures or implants and a second position defined by said distal ends being separated by a degree of expansion defined by the size of an insert positioned therebetween, said degree of expansion thereby forming and maintaining a space for insertion of bone graft material;

one or more inserts each having a proximal end, a distal end, and an internal lumen there between adapted for receipt of a plunger, said one or more inserts adapted to be positioned between said applicator tabs, said one or more inserts having a particular size and shape which acts to define said degree of expansion of said applicator tabs upon insertion therebetween; and a plunger for urging bone graft material along a path defined by said applicator tabs and said one or more inserts.

6. The kit for facilitating placement of bone graft material within or between one or more bony structures or implants according to claim 5 wherein said applicator assembly is constructed and arranged such that said applicator tabs are positioned together at said distal ends thereof to form a generally V-shaped configuration.

7. The kit for facilitating placement of bone graft material within or between one or more bony structures or implants according to claim 5 further including a latching tab formed at the proximal end of said insert for providing a secure connection to said funnel.

8. The kit for facilitating placement of bone graft material within or between one or more bony structures or implants according to claim 5 wherein said one or more inserts are sized and shaped to direct said bone graft material within a space created by the traversal of said applicator tabs from said first closed position to said second position.

* * * * *